United States Patent
Klocek et al.

(10) Patent No.: US 6,735,462 B2
(45) Date of Patent: May 11, 2004

(54) METHOD AND APPARATUS FOR INFRARED IMAGING IN SMALL PASSAGEWAYS

(75) Inventors: Paul Klocek, Dallas, TX (US); Douglas W. Anderson, Richardson, TX (US)

(73) Assignee: Raytheon Company, Waltham, MA (US)

( * ) Notice: Subject to any disclaimer, the term of this patent is extended or adjusted under 35 U.S.C. 154(b) by 360 days.

(21) Appl. No.: 09/747,183

(22) Filed: Dec. 21, 2000

(65) Prior Publication Data

US 2002/0076178 A1 Jun. 20, 2002

(51) Int. Cl.[7] .............................. A61B 6/00; A61B 5/05
(52) U.S. Cl. ........................................ 600/473; 600/407
(58) Field of Search ................................. 600/473, 474, 600/475

(56) References Cited

U.S. PATENT DOCUMENTS

| | | | |
|---|---|---|---|
| 5,704,896 A | | 1/1998 | Fukunishi et al. |
| 5,815,624 A | | 9/1998 | Rosenberg |
| 5,853,370 A | * | 12/1998 | Chance et al. ............. 600/473 |
| 6,032,070 A | * | 2/2000 | Flock et al. ................ 600/473 |
| 6,272,374 B1 | * | 8/2001 | Flock et al. ................ 600/473 |
| 6,397,099 B1 | * | 5/2002 | Chance ....................... 600/473 |
| 6,411,835 B1 | * | 6/2002 | Modell et al. ............. 600/407 |
| 6,529,770 B1 | * | 3/2003 | Grimblatov ................ 600/479 |
| 6,567,690 B2 | * | 5/2003 | Giller et al. ................ 600/473 |

FOREIGN PATENT DOCUMENTS

| | | |
|---|---|---|
| DE | 196 21 652 A1 | 12/1997 |
| WO | WO 00/21279 | 4/2000 |

OTHER PUBLICATIONS

Klocek, et al., "Infrared Fiber Optics", Section 3, "Applications of IR Fiber Optics", SPIE Press, Bellingham, WA, 1989, cover sheet plus pp. 123–147, and Author page.

Klocek, et al., "The Development and Applications of Chalcogenide Infrared Optical Fibers", SPIE Proceedings, vol. 572, 1985., 10 unnumbered pages.

* cited by examiner

Primary Examiner—Thomas Denion
Assistant Examiner—Daniel Robinson
(74) Attorney, Agent, or Firm—Baker Botts 1.L.P.

(57) ABSTRACT

An infrared imaging system (10) includes a catheter (11). The catheter is inserted into a small passageway, such as a blood vein (23), in order to collect infrared information from the vein. The information is refracted by at least one lens (32, 46, 52, 57, 63) in a collecting section (17, 45, 56, 61) of the catheter, and is imaged onto the ends (38) of an array of optical fibers (34). The fibers transmit the information to a relay lens (42), which images the information onto respective detector elements of an infrared detector (12). The infrared detector converts the information received from the relay lens into electrical information, which is transmitted to a circuit (13). The circuit generates electrical data that is transmitted to a display (16), which displays a visible image based on the infrared radiation emitted by the scene.

14 Claims, 7 Drawing Sheets

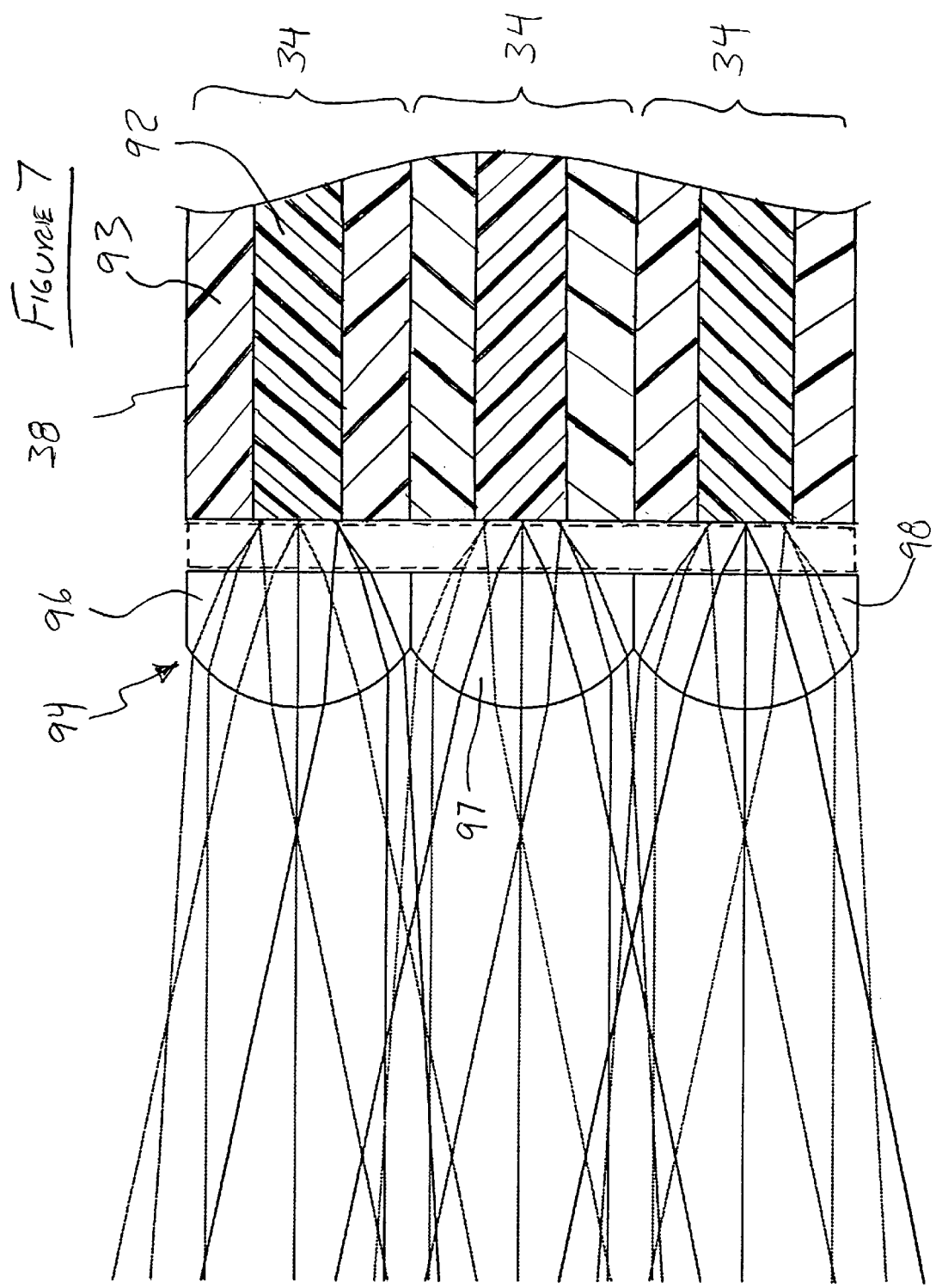

METHOD AND APPARATUS FOR INFRARED IMAGING IN SMALL PASSAGEWAYS

TECHNICAL FIELD OF THE INVENTION

This invention relates in general to infrared imaging and, more particularly, to infrared imaging in a passageway.

BACKGROUND OF THE INVENTION

Thermal imaging has developed rapidly over the past several years. Obtaining information based on temperature differences has proven to be an effective and accurate way to gather information in certain applications. Thermal imaging systems generally include a collecting component, an infrared detector, a circuit, and a display. The collecting component images infrared radiation onto the infrared detector. The infrared detector then generates electrical information that is sent to the circuit. The circuit converts the electrical information into electrical data which is displayed on the display. Thus, the display shows a visible image which represents the infrared radiation collected by the collecting component. These thermal imaging systems have been generally adequate for their intended purposes, but have not been satisfactory in all respects.

A problem with current thermal imaging systems is that they are too large to be used to gather information within the interior of small passageways. In the area of medicine, such passageways include a blood vein or artery. For example, in diagnosing potential heart problems, early detection of weaknesses or blockages of blood veins or arteries is critical. One cause of heart attacks is the presence of lesions within blood veins. The lesions can become inflamed and erupt, introducing debris into the veins which can trigger a heart attack, even when the blockage within veins and arteries is low. When inflamed, the lesions have a higher temperature than surrounding portions of the interior surface of the blood veins, and could thus theoretically be detected by infrared imaging techniques. However, as noted above, existing infrared imaging equipment is too large to be used within a passageway as small as a blood vein.

There are also industrial applications in which thermal imaging within a very small space is of interest, for example for inspection of certain types of equipment. Again, existing infrared imaging systems are too big to be inserted into such small spaces.

A further consideration is that prior systems used an infrared detector that had to be cooled, and the presence of a cooling mechanism makes the overall system relatively expensive.

SUMMARY OF THE INVENTION

From the foregoing, it may be appreciated that a need has arisen for a method and apparatus for infrared imaging in places such as a small passageway. According to the present invention, a method and apparatus are provided to address this need, and involve: transmitting infrared image information through an elongate optical portion from a first end thereof to a second end thereof; collecting infrared image information and supplying it to the first end of the optical portion; and receiving infrared information at a section which includes an infrared image detector and which directs infrared image information from the second end of the optical portion onto the image detector.

BRIEF DESCRIPTION OF THE DRAWINGS

A better understanding of the present invention will be realized from the detailed description which follows, taken in conjunction with the accompanying drawings, in which:

FIG. 7 is a diagrammatic sectional side view of an end portion of an alternative embodiment of the elongate optical portion of FIGS. 1 and 2, showing the ends of three fibers and showing a microlens array.

DETAILED DESCRIPTION OF THE INVENTION

Figure 1:
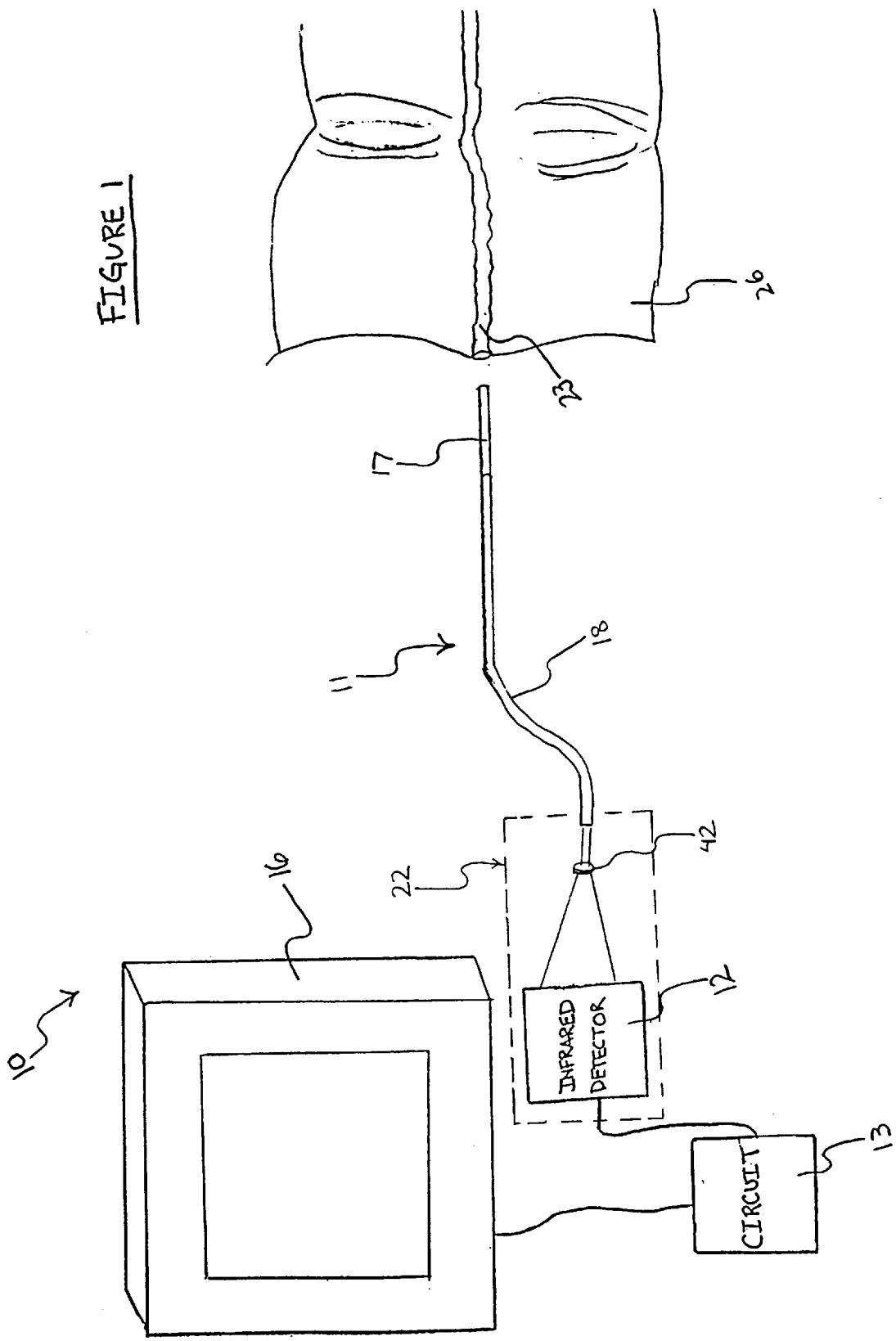
FIG. 1 is a diagrammatic view of an infrared imaging system that embodies the present invention, and a portion of a person's arm.

FIG. 1 is a diagrammatic view showing an infrared imaging system 10, and part of an arm 26 of a person. The infrared system 10 includes a catheter 11, a circuit 13 and a display 16. The catheter 11 can be inserted into a blood vein 23 of a person's arm 26, in order to collect infrared information emitted by a scene which is an interior surface of the vein 23. The infrared information collected by the catheter 11 is far infrared radiation having a wavelength in the range of approximately 8–14 micrometers, but could alternatively be near infrared radiation.

The catheter 11 includes a collecting section 17, an elongate optical portion 18 which is flexible, and an end section 22 which includes an infrared detector 12. The collecting section 17, the elongate optical portion 18, and the end section 22 will be discussed in more detail later in association with FIG. 2.

The infrared detector 12 illustrated in FIG. 1 is an uncooled detector of a known type, which has a 30×30 array of not-illustrated detector elements that detect infrared radiation which impinges on them. In the array, the center to center spacing of the detector elements along the columns and along the rows is 50 $\mu$m. The infrared detector 12 could alternatively be any other suitable infrared detection mechanism. The infrared detector 12 is at an end of the elongate optical portion 18 opposite from the collecting section 17. The infrared detector 12 receives through the elongate optical portion 18 infrared information emitted by the interior of the vein 23. The infrared detector 12 transmits to the circuit 13 electrical information based on the infrared image information it detects. The circuit 13 is of a known type. The circuit 13 generates electrical data corresponding to the electrical information produced by the infrared detector 12. The electrical data is then transmitted from the circuit 13 to a conventional display 16. The display 16 produces a visible image corresponding to the scene observed by the collecting section 17.

Figure 2:
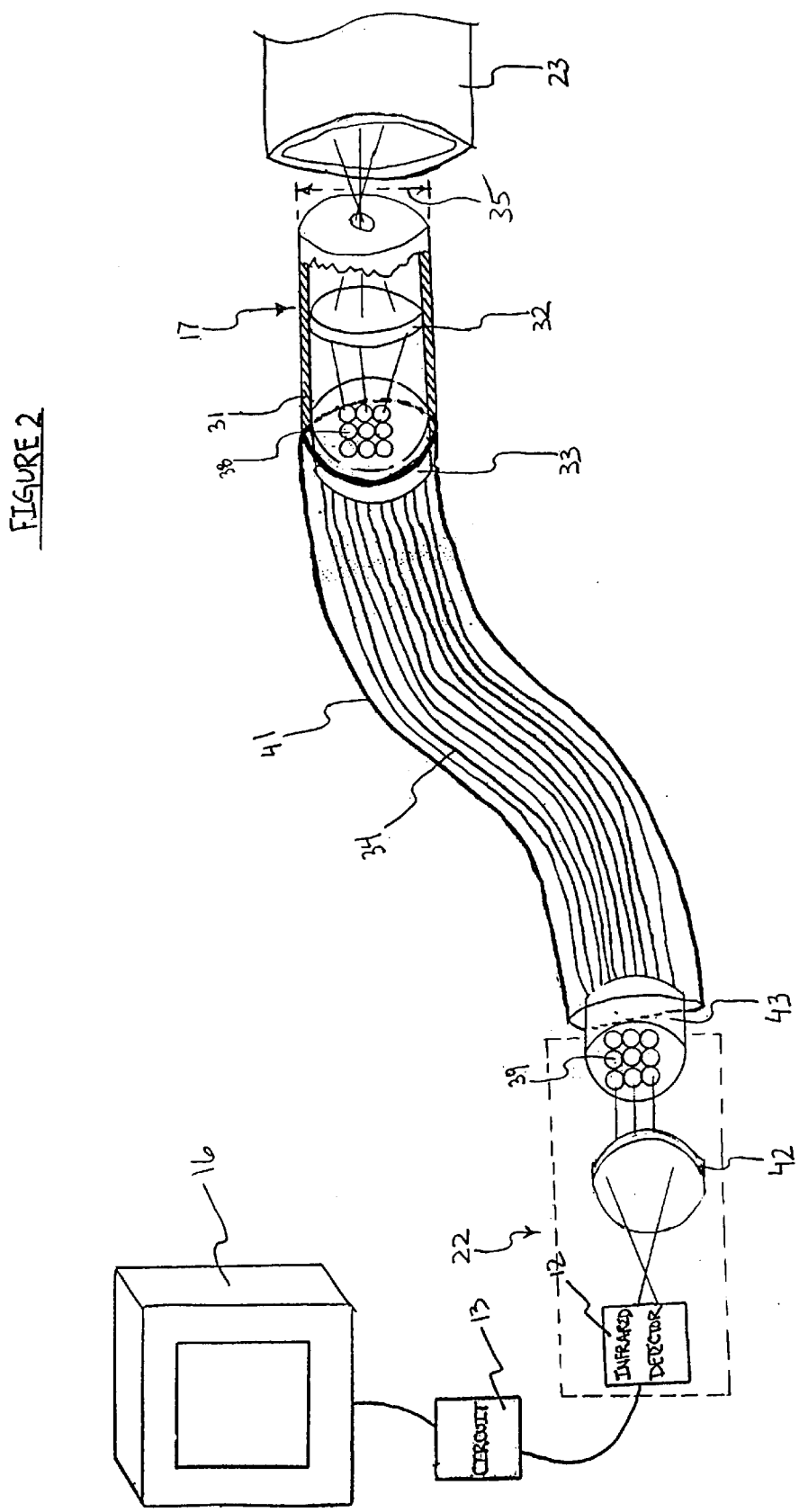
FIG. 2 is a diagrammatic view of the infrared imaging system of FIG. 1 and part of a blood vein, showing details of a collecting section, an elongate optical portion, and an end section of the imaging system.
Figure 3:
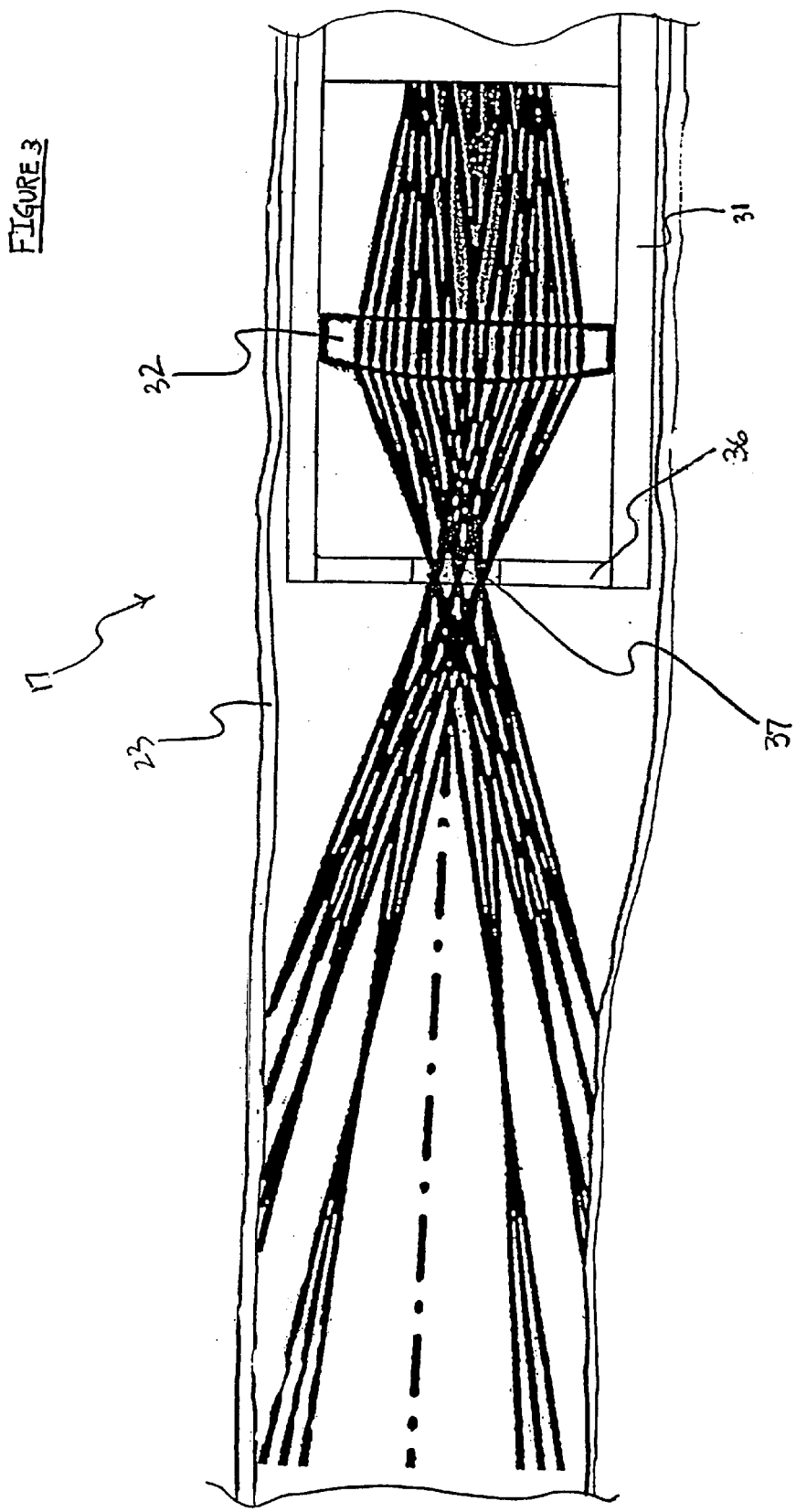
FIG. 3 is a diagrammatic sectional view of the collecting section of the infrared imaging system of FIG. 1, and part of a blood vein.

As shown in more detail in FIGS. 2 and 3, the collecting section 17 includes a sleeve 31 and a lens 32. The collecting section 17 has a diameter 35 which is approximately 2500 to 3000 micrometers. The sleeve 31 is supported at one end on the elongate optical portion 18, and in turn supports an aperture stop 36, an infrared transmissive window 37, and the lens 32. The sleeve 31 is a plastic, cylindrical member that provides a protective outer layer for the collecting section 17. Further, the sleeve 31 has a coefficient of thermal expansion (CTE) selected so that variations in the temperature of the catheter, and thus expansion and contraction of the sleeve 31, have a minimal effect on the operation of the catheter. The aperture stop 36 is a circular, flat part with a hole through it. The aperture stop 36 defines the desired ray bundles for the lens 32, and blocks unwanted infrared energy from reaching the lens 32 and the end portions 38 of the fibers. The protective window 37 is a flat, circular piece of silicon which is disposed in the hole in the aperture stop 36. Alternatively, the protective window 37 could be made of any other suitable infrared transmissive material. The protective window 37 has a center which is co-axial with the center of the lens 32. The protective window 37 provides a physical barrier that prevents particles and debris from entering the sleeve 31 of the catheter 11.

The lens 32 is a wide angle objective lens that refracts infrared information from the scene within the vein 23. The lens 32 is circular, and made of chalcogenide glass of a known type. The lens 32 is supported by the sleeve 31. Alternatively, the objective lens 32 could be made of any other suitable infrared transmissive material that can image infrared information. The lens 32 is positioned within about 1 centimeter of the scene that emits the infrared information imaged by the lens 32. Thus, the distance which radiation travels from the lens 32 to the infrared detector 12 through the optical fibers 34 is several times greater than the distance which radiation travels from the scene to the lens 32.

The lens 32 refracts the infrared information from the vein 23 onto the ends 38 of a bundle of optical fibers 34 that are included in the elongate portion 18. The lens 32 images onto the ends of the fibers an annular region of the interior surface of the vein 23. The lens 32 is telecentric with the fiber bundle in order to maximize efficiency and minimize shading in the resulting image. The optical fibers 34 are flexible coherent optical fibers which each have a core surrounded by a sleeve-like cladding. Each fiber carries a respective portion of the image information, where each such portion corresponds to a respective pixel of the image. In the disclosed embodiment, the cladding of each fiber has an outside diameter of 50 microns, and has an inside diameter of 30 microns, which of course is also the outside diameter of the core. The cladding has an index of refraction of 2.58, and by atomic weight is composed of 28% germanium (Ge), 12% antimony (Sb), and 60% selenium (Se). The core has an index of refraction of 2.60, and by atomic weight is composed of 30% germanium (Ge), 10% antimony (Sb), and 60% selenium (Se). The diameter of the core, in relation to the wavelengths of the infrared radiation of interest, causes each fiber to approach single mode operation, increasing the potential for problems of crosstalk between adjacent fibers. The foregoing compositions of the core and the cladding, as well as the ratio of their diameters, have been selected so that problems of crosstalk will be negligible.

A lubricant such as a polytetrafluoroethylene (TEFLON™) coating is applied to the exterior surfaces of the optical fibers 34, in order to reduce friction between the optical fibers 34. The optical fibers 34 each have two end portions 38 and 39 which are respectively disposed at the collecting section 17 and the end section 22. The bundle of fibers defines a 30×30 fiber bundle array but, for clarity in the drawings, the 30×30 array is shown diagrammatically in FIGS. 1 and 2 as a 3×3 array. Adjacent fiber end portions 38 are in tangential contact with each other, and adjacent end portions 39 are also in tangential contact. The center to center spacing between the ends 38 of the optical fibers 34 is 50 μm, and the center to center spacing between the ends 39 of the fibers is also 50 μm. The ends 38 of the optical fibers 34 are held in position with respect to each other by a circular element 33, and the ends 39 are held in position by a similar circular element 43. The elements 33 and 43 each have a 3×3 array of holes provided therethrough, and each hole receives the end 38 or 39 of a respective optical fiber 34. The elements 33 and 43 are made of a known chalcogenide glass that can be etched. Alternatively, the elements 33 and 43 could be made of any other suitable material.

The two opposite ends of a flexible sheath 41 are respectively sealingly coupled to the elements 33 and 43. The sheath 41 is a thin polymer sleeve that provides a protective layer for the optical fibers 34, which keeps particles out of the fibers in order to simplify sterilization of the catheter 11. Alternatively, the sheath 41 could be made of any other suitable material. The end of the sheath 41, opposite the lens 32, is associated with the end section 22.

The end section 22 includes an infrared transmissive relay lens 42. The relay lens 42 is a circular lens made of chalcogenide glass, but could alternatively be made of any other suitable infrared transmissive material. The relay lens 42 is disposed between the ends 39 of the optical fibers 34 and the infrared detector 12. The lens 42 is telecentric with the fiber bundle in order to maximize efficiency and minimize shading in the resulting image. The relay lens 42 directs the infrared information received from each optical fiber 34 onto a respective detector element of the infrared detector 12.

Figure 4:
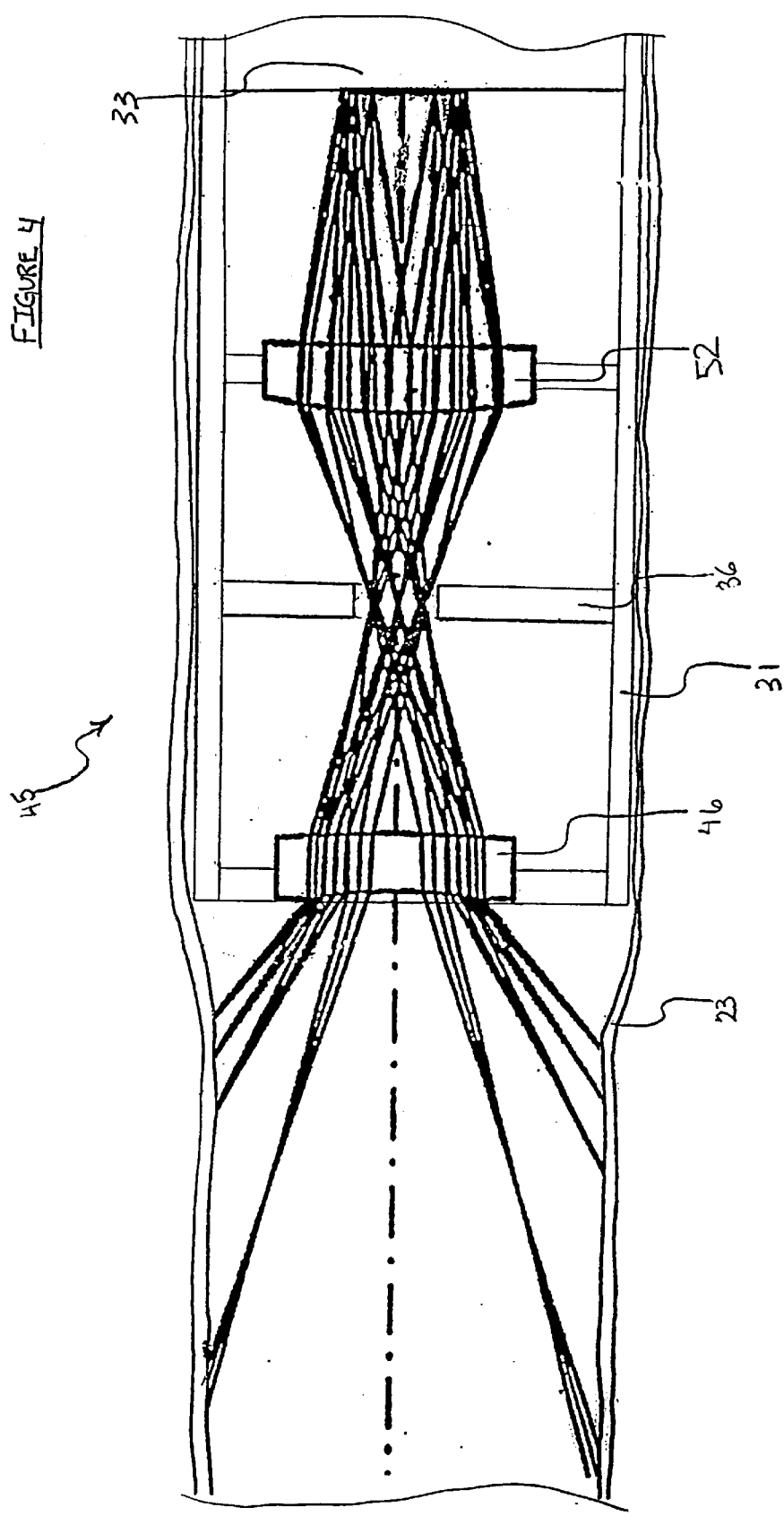
FIG. 4 is a diagrammatic sectional view similar to FIG. 3, but showing an alternative embodiment of the collecting section, and part of a blood vein.

FIG. 4 shows a collecting section 45 which is part of an alternative embodiment of the present invention. The alternative embodiment is identical to the embodiment described in association with FIGS. 1–3, except for the collecting section 45. The collecting section 45 includes a wide angle objective lens 52, the sleeve 31, and an additional lens 46. The collecting section 45 has a diameter which is approximately 2500–3000 micrometers. The objective lens 52 is supported by the sleeve 31. The objective lens 52 is circular and made of chalcogenide glass. Alternatively, the objective lens 52 could be made of any other suitable infrared transmissive material.

The aperture stop 36 is supported by the sleeve 31 between the additional lens 46 and the objective lens 52. The additional lens 46 is made of chalcogenide glass, but could alternatively be made of any other suitable infrared transmissive material. The additional lens 46 is supported within an opening provided through a member 54 disposed at the outer end of the sleeve 31. The member 54 and the additional lens 46 act as a protective window, providing a barrier that prevents particles and debris from entering the sleeve 31 of the catheter 11. The additional lens 46 is positioned within about 1 centimeter of the scene that emits infrared information supplied to the catheter 11. The additional lens 46 cooperates with the wide angle objective lens 52 to collect infrared information from a scene which is the interior of the vein 23. The infrared information that passes through the additional lens 46 and the objective lens 52 is imaged onto the ends 38 (FIG. 2) of the optical fibers 34.

Figure 5:
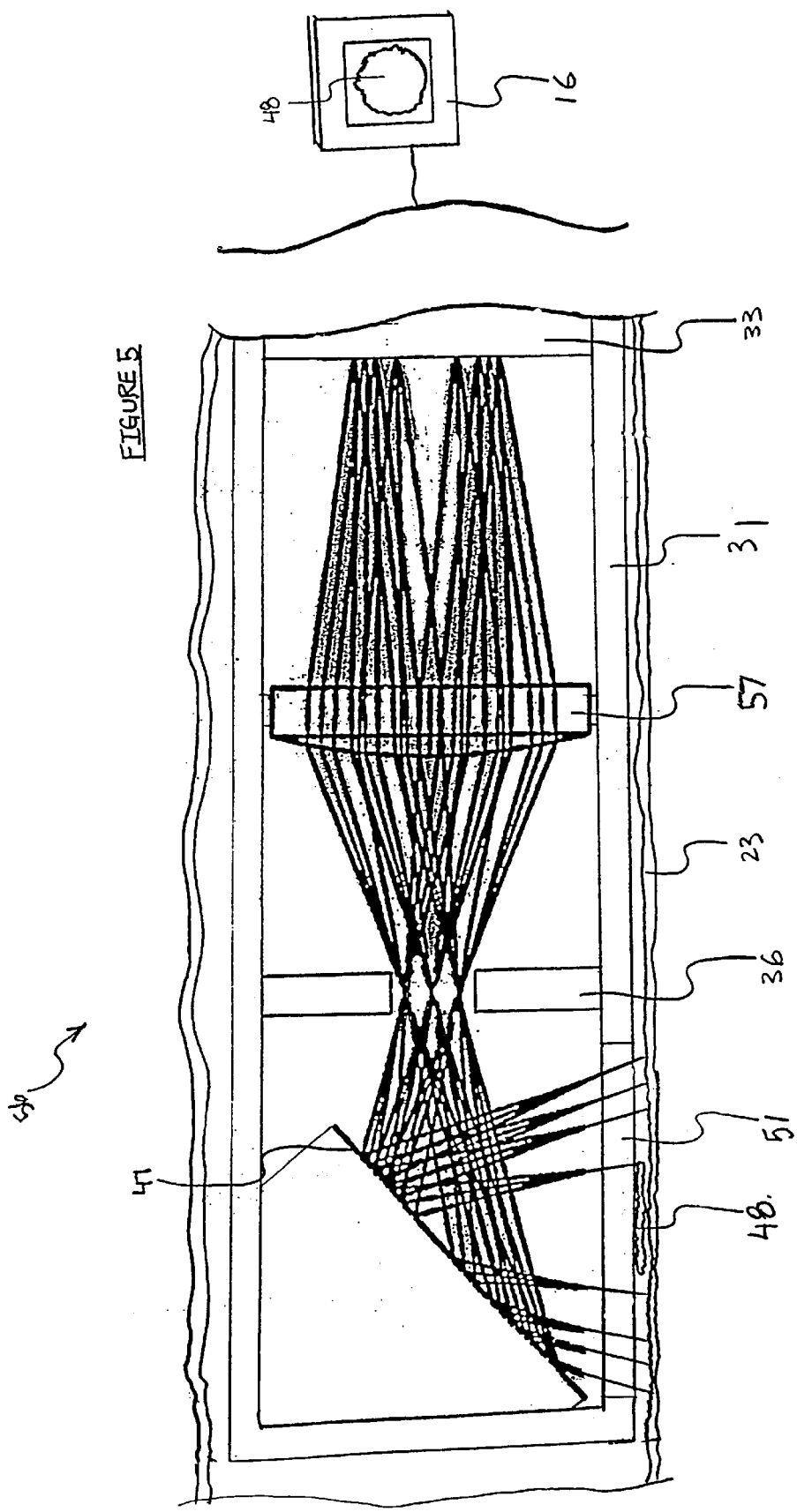
FIG. 5 is a diagrammatic sectional view similar to FIG. 3, but showing a display and another alternative embodiment of the collecting section, and showing part of a blood vein.

FIG. 5 is a diagrammatic sectional view similar to FIG. 3, but showing a collecting section 56 which is part of another alternative embodiment. This alternative embodiment is identical to the embodiment described in association with FIGS. 1–3, except for the collecting section 56. The collecting section 56 includes a wide angle objective lens 57, the sleeve 31 and a mirror 47. The collecting section 56 has a diameter which is approximately 2500–3000 micrometers. The objective lens 57 is a circular part that is made of chalcogenide glass and supported by the sleeve 36. Alternatively, the objective lens 57 could be made of any other suitable infrared transmissive material. The sleeve 31 includes on one side thereof near its outer end an infrared transmissive window 51. The protective window 51 extends a greater axial length than the mirror 47, permits entry of infrared radiation, and provides a barrier that prevents particles and debris from entering the sleeve 31.

The aperture stop 36 is disposed between the mirror 47 and the objective lens 57. The aperture stop 36 defines the desired ray bundles for the lens 57, and blocks unwanted infrared energy from reaching the lens 57 and the end portions 38 of the fibers. The mirror 47 is made of any suitable material that can reflect infrared radiation. The mirror 47 is supported by the sleeve 31 and by a wall 59 fixedly disposed at the outer end of the sleeve 31. The mirror 47 is positioned within about 1 centimeter of an object 48 that emits infrared information. Although the mirror 47 shown in FIG. 5 is planar, it could optionally be convexly curved so as to provide a degree of magnification power. The mirror 47 cooperates with the wide angle objective lens 57 to collect infrared information from the vein 23, including the object 48. Infrared information reflected by the mirror 47 passes through the objective lens 57, and is then imaged onto the ends 38 (FIG. 2) of the optical fibers 34.

Figure 6:
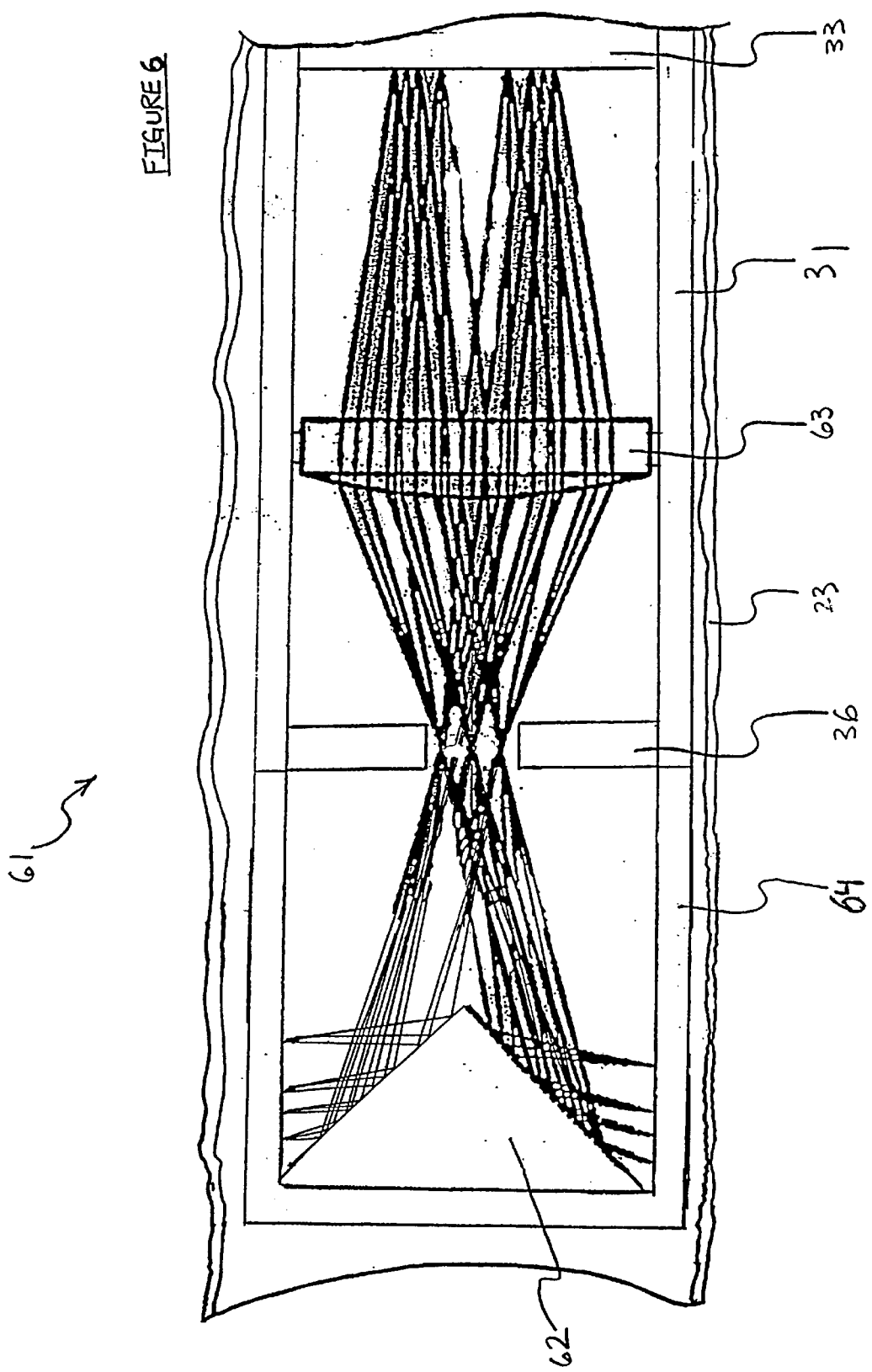
FIG. 6 is a diagrammatic sectional view similar to FIG. 3, but showing still another alternative embodiment of the collecting section, and part of a blood vein.

FIG. 6 shows yet another alternative embodiment of the present invention. The alternative embodiment is very similar to the embodiment described in association with FIGS. 1–3, except for a collecting section 61 thereof which collects infrared information. The collecting section 61 includes a wide angle objective lens 63, the sleeve 31 and a conical member 62. The collecting section 61 has a diameter which is approximately 2500–3000 micrometers. The objective lens 52 is circular, and made of chalcogenide glass. The lens 63 is supported by the sleeve 31. Alternatively, the objective lens 52 could be made of any suitable infrared transmissive material. The sleeve 31 also supports a cup-like infrared transmissive window 64 that supports the conical member 62, and that extends a greater axial length than the conical member 62. The window 64 allows infrared radiation to be simultaneously collected from 360°. The protective window 64 is made of a suitable infrared transmissive material. The protective window 64 provides a barrier that prevents particles and debris from entering the collecting section 61.

The aperture stop 36 is disposed between the conical member 62 and the objective lens 63. The aperture stop 36 defines the desired ray bundles for the lens 63, and blocks unwanted infrared energy from reaching the lens 63 and the end portions 38 of the fibers. The conical member 62 is made of any suitable known material that can reflect infrared radiation. The conical member 62 is positioned within about 1 centimeter of the scene that emits infrared information. The conical member 62 cooperates with the wide angle objective lens 63 to collect infrared information from an annular surface region within the interior of the vein 23. The infrared information reflected by the surface of the conical member 62 to the objective lens 63 is imaged onto the ends 38 (FIG. 2) of the optical fibers 34.

FIG. 7 is a diagrammatic sectional side view of an end portion of an alternative embodiment of the elongate optical portion 18 of FIGS. 1 and 2. In FIG. 7, the end portions 38 of three of the fibers 34 are shown. As discussed above, each fiber 34 includes a core 92 surrounded by a cladding 93. A microlens array 94 is supported on the ends of the fibers 34 by a spacer element 95, which is shown in broken lines in FIG. 7 for clarity, and which can be made from any suitable material that is transparent to infrared radiation. Instead of the spacer element 95, an air gap of equal thickness could be provided between the microlens array 94 and the ends of the fibers 34, for example by providing some other suitable mechanical arrangement to fixedly support the array 94 in a spaced relationship with respect to the ends of the fibers.

The microlens array 94 includes a respective microlens portion in alignment with each fiber 34, three of the microlens portions being visible in FIG. 7 at 96, 97 and 98. Each microlens portion 96–98 receives the infrared radiation which would otherwise impinge on the core and cladding of the associated fiber 34, and concentrates all of this radiation onto only the core of the associated fiber, so that substantially all of this radiation enters the core and is propagated through the fiber. It will be recognized that, without the microlens portions 96–98, the portion of the incident radiation which impinges on the core would in fact enter the core, but the portion of the radiation which impinges on the cladding would be lost through reflection or absorption. The microlens array 94 thus significantly increases the efficiency of the system. The microlens array 94 supplements rather than replaces the other lenses in the collecting section, such as the lens shown at 32 in the embodiment of FIGS. 1–3.

In the embodiment of FIG. 7, the end of the elongate optical portion remote from the illustrated end is not shown, but is a mirror image of the illustrated end, and in particular includes a further microlens array supported by a further spacer element. The microlens portions of the further microlens array would each take the radiation traveling through the core of a respective fiber, and deconcentrate this energy in a manner opposite to the manner in which it was concentrated by a respective microlens portion of the microlens array 94. In effect, the microlens array 94 provides a faster f-number than the lens or lenses of the collecting section can provide by themselves, and then the further microlens array at the opposite end of the fibers has the effect of changing the f-number back to a slower value. The further microlens array supplements rather than replaces any lens arrangement in the region of the infrared detector, such as the relay lens shown at 42 in FIGS. 1–2.

A description will now be provided of the operation of the infrared imaging system 10 of FIGS. 1–4. Infrared information is emitted by a scene within the blood vein 23 of a person's arm 26. As shown in FIGS. 1, 2, and 3, this infrared information passes through the window 37 in aperture stop 36, and the aperture stop filters out stray radiation that is not part of the infrared information of interest. Then, the infrared information passes through the lens 32, which images the infrared information onto the ends 38 of the optical fibers 34. The optical fibers 34 of the elongate optical portion 18 transmit the infrared image information from the collecting section 17 to the end section 22. Each fiber carries a respective portion of the overall image, each such portion corresponding to a respective pixel in a 30×30 array of pixels making up the image.

The end section 22 receives the infrared image information from the fibers. The infrared image information from the optical fibers 34 passes through the relay lens 42 and is imaged onto the infrared detector 12. The infrared radiation from each fiber is directed onto a respective one of the detector elements of the infrared detector. As noted above, the fibers and the detector elements have the same center to center spacing, and it would thus be possible to omit the relay lens 42, if the fibers are each accurately physically aligned with a respective detector element. The infrared detector 12 converts the infrared image information into electrical information that is transmitted to the circuit 13. The circuit 13 generates electrical data corresponding to the infrared image information received by the collecting section 17. The electrical data is then transmitted from the circuit 13 to the display 16. The display 16 produces a visible image of the scene being observed by the collecting section 17.

The alternative embodiments illustrated in FIGS. 4–6 each operate in a manner similar to the embodiment described above in association with FIGS. 1–3, except that the collecting section of each operates differently. FIG. 4 illustrates how the additional lens 46 cooperates with the wide angle objective lens 52 to collect infrared image information of a scene within the vein 23. The aperture stop 36 defines the desired ray bundles for the lens 52, and blocks unwanted infrared energy from reaching the lens 52 and the end portions 38 of the fibers. The desired infrared information which has passed through the aperture stop 36 is then refracted by lens 52 and imaged onto the ends 38 (FIG. 2) of the optical fibers 34. The infrared image information is then transmitted and displayed in the same manner described above with respect to FIGS. 2 and 3.

FIG. 5 illustrates how the mirror 47 cooperates with the wide angle objective lens 57 to collect infrared information of the object 48 within the vein 23. The aperture stop 36 defines the desired ray bundles for the lens 57, and blocks unwanted infrared energy from reaching the lens 57 and the end portions 38 of the fibers. The desired infrared information which has passed through the aperture stop 36 then passes through the objective lens 57 and is imaged onto the ends 38 (FIG. 2) of the optical fibers 34. The infrared image information is then transmitted and displayed in the same manner described above with respect to FIGS. 2 and 3.

FIG. 6 illustrates how the reflective conical member 62 cooperates with the wide angle objective lens 63 to collect infrared information of a scene within the vein 23. Infrared information from 360° is reflected by the surface of the conical member 62. The aperture stop 36 defines the desired ray bundles for the lens 63, and blocks unwanted infrared energy from reaching the lens 63 and the end portions 38 of the fibers. The objective lens 63 images the desired infrared information onto the ends 38 (FIG. 2) of the optical fibers 34. The infrared image information is then transmitted and displayed in a manner similar to that described above with respect to FIGS. 2 and 3.

The present invention provides a number of technical advantages. One such technical advantage is the capability to gather infrared information from a small, otherwise inaccessible passageway. In the area of medicine, such a passageway could be a vein, an artery, or any other small or narrow cavity which produces thermal energy sought to be examined. The present invention allows the thermal energy emitted from the interior of the passageway to be viewed on a display. This provides an opportunity to detect subject matter which would otherwise be difficult to detect, such as lesions within the interior of a vein or artery.

Although one embodiment has been illustrated and described in detail, it should be understood that various substitutions and alterations can be made therein without departing from the scope of the present invention. For example, while the infrared imaging system has been described above with respect to a medical catheter, it will be recognized that the infrared imaging system could be used in a variety of other applications. For example, the infrared imaging system could be used in an endoscope, a probe, or as an attachment to any of a variety of surgical instruments. In addition, the infrared imaging system according to the invention could be used in certain industrial applications where thermal imaging is needed within a small space. Other substitutions and alterations are also possible without departing from the spirit and scope of the present invention, as defined by the following claims.

What is claimed is:

1. An invasive apparatus for infrared imaging in a small passageway comprising:

an elongate optical portion which has first and second ends and which can transmit infrared image information from said first end to said second end;

a first section which collects infrared image information and supplies it to said first end of said optical portion, the infrared image information collected from within the passageway; and a second section which includes an infrared image detector that receives infrared image information from said second end of said optical portion wherein said optical portion is flexible plurality of fibers whereby each of said optical fibers includes two end portions which are respectively disposed at said first and second ends and wherein each of said plurality of fibers includes a cladding and includes a core disposed within said cladding; and including a plurality of lens portions which are each associated with and supported in alignment with a respective said fiber at said first end of said elongate portion, and which each concentrate onto said core of said associated fiber the radiation which would otherwise impinge on said cladding of associated fiber.

2. An invasive apparatus according to claim 1, including a plurality of further lens portions which are each associated with and supported in alignment with a respective said fiber at said second end of said elongate portion, and which each receive and deconcentrate radiation from the core of said associated fiber.

3. An invasive apparatus according to claim 2, wherein said optical fibers each have a coating which reduces friction between said optical fibers.

4. An invasive apparatus according to claim 2, wherein said first section includes an aperture stop, and wherein infrared image information collected by said first section passes through said aperture stop.

5. An invasive apparatus according to claim 2, further comprising a sheath, said sheath sealing said optical fibers within said sheath between said first and second ends to form a protective barrier for said optical fibers.

6. An invasive apparatus according to claim 5, wherein said first section includes a sleeve, said sleeve being supported by said first end of said optical portion, and said sleeve supporting said first section.

7. An invasive apparatus according to claim 6, wherein said first section includes an objective lens supported by said sleeve, said objective lens imaging infrared information collected by said first section.

8. An invasive apparatus according to claim 7, wherein said objective lens is configured to operate within approximately one centimeter of a scene that emits infrared information supplied to said first end of said optical portion, and wherein the distance that radiation travels from said first end to said infrared image detector through said optical portion is substantially longer than a distance that radiation travels from said scene to said first end.

9. An invasive apparatus according to claim 7, wherein said first section includes a conical reflective surface supported by said sleeve, said reflective surface reflecting to said objective lens infrared information being supplied by said first section to said first end of said optical portion.

10. An invasive apparatus according to claim 7, wherein said first section includes an additional lens supported by said sleeve, said additional lens cooperating with said objective lens to supply infrared image information to said first end of said optical portion.

11. An invasive apparatus according to claim 7, wherein said first section includes a reflective surface supported by said sleeve, said reflective surface reflecting infrared information to said objective lens of said first section.

12. An invasive apparatus according to claim 1, wherein said infrared image detector is an uncooled detector and includes an array of detector elements, and wherein infrared radiation traveling through each of said fibers is directed onto a respective said detector element.

13. An invasive apparatus according to claim 1, wherein said first section and said optical portion each have a maximum transverse dimension less than approximately 3000 micrometers.

14. An invasive apparatus according to claim 1, wherein said second section includes a relay lens, said relay lens being positioned optically between said infrared image detector and said second end, and directing infrared image information received from said second end onto said infrared image detector.

* * * * *